United States Patent [19]

Motoyama et al.

[11] Patent Number: 4,756,922

[45] Date of Patent: Jul. 12, 1988

[54] POWDER COATING METHOD

[75] Inventors: Shimesu Motoyama, Asaka; Seiichi Umeda, Tsurugashima; Hiroaki Ogishima, Tokorozawa; Sashiro Motegi, Ageo, all of Japan

[73] Assignees: Freund Industrial Co., Ltd.; Kirin Brewery Co., Ltd., both of Tokyo, Japan

[21] Appl. No.: 47,779

[22] Filed: May 8, 1987

[30] Foreign Application Priority Data

May 12, 1986 [JP] Japan .................................. 61-108352

[51] Int. Cl.$^4$ ............................................... B05D 7/24
[52] U.S. Cl. ........................................ 427/4; 47/57.6; 47/DIG. 11; 427/180; 427/212
[58] Field of Search ........................... 427/4, 180, 212; 47/57.6, DIG. 11

[56] References Cited

U.S. PATENT DOCUMENTS

| | | | |
|---|---|---|---|
| 1,764,888 | 6/1930 | Raleigh | 47/57.6 |
| 2,614,945 | 10/1952 | Krisan | 427/212 |
| 3,687,699 | 8/1972 | Prosser | 427/180 |
| 4,197,330 | 4/1980 | Grimm | 427/4 |
| 4,359,492 | 11/1982 | Schlademan | 427/180 X |
| 4,495,724 | 1/1985 | Kirkland et al. | 47/57.6 |
| 4,583,320 | 4/1986 | Redenbaugh | 47/57.6 |

FOREIGN PATENT DOCUMENTS

| | | | |
|---|---|---|---|
| 678924 | 1/1964 | Canada | 427/4 |
| 743738 | 1/1956 | United Kingdom | 427/180 |

Primary Examiner—Shrive P. Beck
Attorney, Agent, or Firm—Kane, Dalsimer, Sullivan, Kurucz, Levy, Eisele and Richard

[57] ABSTRACT

A method in which a plant meristematic tissues which retain aqueous liquid on their surfaces are mixed with fine powder, thereby forming powder-coated bodies to which fine powder is adhered at the periphery thereof, so that meristematic tissues are separated from each other. A quantity of water or a liquid mainly consisting of water large enough to make fine powder adhere to the surfaces of the meristematic tissues which can grow into entire plant bodies directly or after they have passed through differentiation and organogenesis. The meristematic tissues are mixed with the fine powder which does not indicate adhesiveness at least during the mixing process. This mixing process is effected in such a manner that the powder is adhered to the tissues by gently shaking or agitating them without applying excessive shearing stress to the meristematic tissues.

5 Claims, No Drawings

POWDER COATING METHOD

BACKGROUND OF THE INVENTION

(1) Field of the Invention

The present invention relates to a technique for facilitating the handling of plant meristematic tissues.

(2) Related Art Statement

The breeding of plants has been conventionally achieved by fixing superior characteristics acquired by crossing or the induction of mutation as a specific variety (fixed variety). In addition, techniques such as gene recombination and cell fusion have recently led to an employment.

However, anyone of the techniques requires, for particularly an annual plant, the process in which seeds are gathered from parent plants possessing superior characteristics and these are sown in order to obtain offsprings having the same characteristics as these parent plants. Such a breeding method with seeds requires much labor and time and a particular technique for producing a fixed variety and always involves the danger that the characteristics of the fixed variety once produced will deteriorate as a result of natural crossing.

When a useful variety is established as an $F_1$ hybrid or obtained by a specific chromosomal pattern such as aneuploidy, heterozygosis of structural mutation, or triploidy, it is substantially impossible to cause certain characteristics to be inherited in the coming generation by seed propagation. In these circumstances, it is necessary to gather new seeds by crossing parent plants for each generation, or to obtain seeds by means of a particular treatment. These methods are complicated and, in some cases, involve the possibility of creating an extremely undesirable situation in that it is necessary to depend upon the supply of useful seeds from a particular institution.

Furthermore, propagation methods with seeds require much labor and time and involve disadvantage in being restricted by the weather and the type of land employed.

A technique of vegetative propagation has been developed for the purpose of overcoming the abovementioned disadvantages, in which meristematic tissues such as somatic embryo, adventitious bud, shoot primordium, or callus which are obtained by culturing parts of the tissue of plant bodies are further cultured to encourage shooting and obtain a plant body. Although in some cases this method causes a change in the number of chromosomes, by selecting the conditions, it is possible to obtain a clone having completely the same character as that of the original plant, whereby it is possible in principle to breed from one parent plant a large number of offsprings for many generations without limit.

These types of meristematic tissues are made by culturing plant tissues or cells in a liquid or solid medium under suitable conditions with respect to nutrients, hormones, temperature and so on.

However, with regard to meristematic tissues made in this manner, there is a technical problem in growing a young plant from the meristematic tissue, which provides one of bottlenecks in the development of the technique on usage of the meristematic tissue. That is, to grow a young plant after the process of the tissue culture, a process is necessary in which the meristematic tissues are separated individually or into an assembly each consisting of a few meristematic tissues in some case, and the meristematic tissue separated then must be carried to and set in the place where the young plant grows up.

The mechanical strength of a meristematic tissue is less than that of a natural seed, and the tissues generally adhere each other because of moisture on their surfaces. Therefore, it is an extremely complicated task to separate the tissues individually and carry them to the process of growing up without any damaging to the tissues. To effect these operations without any damaging to the tissues, it is inevitable under the existing circumstances that meristematic tissues are disentangled and separated individually by hand before being carried to the process of growing up. This is far from being an industrial mass production technique, and is inefficient and laborious.

Methods of realizing a process of growing up meristemsatic tissues other than that in which naked meristematic tissue is used have been proposed, such as that disclosed in Japanese Patent Laid-Open No. 59-102308 in which meristematic tissue is encapsulated in a gel matrix, and that disclosed in Japanese Patent Application No. 60-277695 which corresponds to U.S. application Ser. No. 939,514 filed Dec. 9, 1986 in which meristematic tissue is coated so that it is easy to handle, and in that form, the meristematic tissue can be sown directly in a field. In these cases also, it is necessary to previously separate the tissues individually. In addition, it is difficult to perform the above treatments, since mechanical effects such as friction and shock inevitably occur in the process in which the meristematic tissue is encapsulated in a gel matrix or is coated with certain material, which tend to damage the meristematic tissue.

To coat meristematic tissues, it is preferable to employ a tumbling type or a fluidizing type of coating apparatus for production on an industrial scale. However, the coating work performed by using one of these types of apparatus often involves a drying process, so that water contained in the meristematic tissue is evaporated during this process, and there is a risk of the meristematic tissue dying. The meristematic tissue also tends to die while being dried if it is not speedily carried to the next process after it has been made by liquid cultivation and is separated from the liquid culture medium. For this reason also, it is difficult to handle meristematic tissue in a conventional process.

SUMMARY OF THE INVENTION

It is an object of the present invention to provide a method capable of facilitating the handling of meristematic tissues.

It is another object of the present invention to provide a method which makes it possible to deal with meristematic tissues on an industrial scale.

To this end, the present invention provides a method in which a fine powder which does not indicate adhesiveness, at least during a mixing process, is mixed with meristematic tissues which retain on their surface enough aqueous liquid to enable the fine powder to adhere, so that the fine powder adheres to the periphery of the meristematic tissues, thereby forming powder-coated bodies.

In a method in accordance with the present invention, each meristematic tissue is coated with fine powder and separated from each other under moderate conditions, and the mechanical strength and the size of each tissue is increased by the effect of the adhered powder, thereby facilitating the handling of meristematic tissues. Therefore, in a subsequent encapsulating or coating process, the meristematic tissues can readily be dealt with or else planted in that form.

A powder-coated body obtained by the method in accordance with the present invention is capable of retaining the water content of meristematic tissues and enables the meristematic tissues to endure several hours during which the tissues are carried to the next process. When the powder-coated body is further coated, it is also possible to facilitate a drying process thereafter while retaining the water content of the meristematic tissue in the powder-coated body.

The above effects ensure that it is possible to handle meristematic tissues on an industrial scale.

Other and further objects and features of the present invention, other than those described above, will become clear upon reading the following description and the appended claims.

The powder coating method in accordance with the present invention will be described below in detail.

The meristematic tissue which is the object of the present invention is a tissue which can grow into an entire plant body directly or after it has passed through differentiation and organogenesis, but includes no seeds. More concretely, somatic tissue, zygotic tissue and germ line tissue can be used as the meristematic tissue. Somatic tissue comprises meristematic tissues such as those expressed as definite bud, adventitious bud, somatic embryo, shoot primordium, multiple-shoot body, protocorm-like body, green spot, and so on. The technique in accordance with the present invention is also effective when applied to pregerminated or germinated seed because it is possible to effectively protect a budding portion.

The kind of plant utilized in accordance with the present invention is not particularly limited, and any kind of plant may be applicable so long as it is possible to obtain a meristematic tissue from it. Examples of plant species having great practicability are: major crops such as rice, wheat, barley, corn, and soybean; vegetables such as celery, parsley, lettuce, cauliflower, carrot, eggplant, tomato, onion, garlic, ginger, strawberry, watermelon, and asparagus; industrial crops such as rape, sugar cane, sugar beet, and tobacco; medical plants such as belladonna, ginseng, and fennel; and ornamental plants such as chrysanthemum, gladiolus, lily, amaryllis, geranium, begonia, African violet, fern, poinsettia and orchid.

The method of the present invention will be described below by way of examples. In the first place, meristematic tissues obtained by a tissue culture process are separated from the liquid medium by an ordinary means such as decantation, filtration or centrifugation and are thereafter rinsed with water as desired. In order to carry out the powder coating, the meristematic tissue needs to have a suitable quantity of aqueous liquid on its surface. Therefore, when the quantity of aqueous liquid retained on the surface of the tissue is too large, it is necessary to remove a part of it by, for example, blasting air to it. When the quantity of aqueous liquid is insufficient, it is necessary to add a desired quantity of aqueous liquid to it.

In this case, a suitable quantity of aqueous liquid is not fixed, and it differs depending on the kind of meristematic tissue, the kind of powder employed, and powder-coating conditions. In any case, it is necessary to prevent the tissue from being excessively dried. It is sufficient to maintain a quantity of aqueous liquid on the surface of the meristematic tissue large enough to make powder adhere to the surface of the meristematic tissue. The above aqueous liquid is a liquid which mainly consists of water and which may simply be water such as rinsing water as well as liquid culture medium having various nutrients. In a word, it is sufficient for the surface of the meristematic tissue to be supplied with a quantity of water large enough to make powder adhere thereto.

Next, fine powder which does not indicate adhesiveness, at least during a mixing process, is mixed with an aggregate consisting of at least two meristematic tissues which retain on their surfaces a suitable quantity of aqueous liquid. Fine powder of this kind may be formed from a substance which is not water-soluble or from a substance which is slightly water-soluble but does not include adhesivenss at least during a mixing process by its solubility or swelling property with water. If powder shows adhesiveness, tissues are agglomerated with each other into a lump to make it impossible to separate the tissues each other.

Examples of such substances are: minerals such as talc, kaolin, pyrophylite, montmorillonite, vermiculite, chlorite, zeolite, perlite, and bentonite; inorganic salts such as calcium carbonate, calcium sulfate, aluminum silicate, calcium silicate and calcium phosphate; metals; oxides such as silicon dioxide, titanium dioxide and magnesium oxide; metal hydroxide such as aluminum hydroxide; ceramics such as silicon carbide, silicon nitride; high-molecular compounds such as starch, cellulose, protein, wood flour, carboxymethylcellulose (acid type), carboxymethylcellulose calcium, low-substituted hydroxypropyl cellulose, fully hydrolyzed polyvinyl alcohol and synthetic resins such as polyethylene, polypropylene, polystyrene, polyvinyl chloride, urea resin, phenol resin, ABS resin and acryl resin; solid wax and wax-like substances such as carnauba wax, bees wax, calcium stearate, magnesium stearate, stearic acid; carbon; diatom earth or dried soil, and the like. Fine powder in accordance with the present invention may be prepared by mixing more than one of these materials at a suitable ratio. The particle size of fine powder formed from these materials is preferably smaller than 100 mesh.

To make the fine powder adhere to meristematic tissues by mixing, it is preferable to powder the material on the tissues by gently shaking or agitating them without applying excessive shearing stress to the meristematic tissues. This is effected by, for instance, a method of applying small vibration to the meristematic tissues and the powder in a container with a flat bottom by means of a vibrator or the like, a method of applying horizontal vibration by means of a sieving machine or the like, a method of slowly rotating them in a mixer such as a V-typed mixer or a diamond-type mixer, or a method of slowly agitating by using a ribbon blender or the like. However, the present invention is not limited to these methods. In any case, it is not preferable to apply large shearing stress to the meristematic tissues, since such a force causes the meristematic tissues to be damaged, obstructs separation, or causes agglomeration.

DESCRIPTION OF THE PREFERRED EMBODIMENTS

The present invention will be described below by way of examples thereof with reference to a comparison example, but it goes without saying that the present invention is not limited to these examples.

[Example 1]

Somatic embryos (meristematic tissues) of a carrot obtained by a liquid culture method, as described in Kamada and Harada, Z. Pflanzenphisiol. 91: 453–463, (1979), were separated from the liquid culture medium by filtration; about 20 g of somatic embryo thereby obtained were laid generally flat in a bat; and about 50 g of talc (fine powder) was sprinkled thereon, thereafter gently vibrating the bat for 5 minutes. The somatic embryos and the powder were thereafter sieved by a 149 micron mesh so as to remove excessive talc, thereby obtaining powder-coated bodies. Each powder-coated body thus obtained has one somatic embryo in it and could be easily handled. Also each powder-coated body has an improved mechanical strength. After the powder-coated bodies obtained had been coated with lactose by employing a centrifugal tumbling granulating and coating machine, the somatic embryos were not damaged and alive even after they were dried during coating. The somatic embryos coated in this manner were cultured by using a 1/2 MS medium, described in Murashige and Skoog, Physiol. Plant. 15: 473–497, (1962), and 17 out of 18 embryos germinated. On the other hand, somatic embryos which had not been powder-coated were directly coated in the same manner and were damaged severely or died after being dried during coating. The germination ratio was low; only 9 out of 18 embryos germinated.

[Comparison Example 1]

Powder of hydroxypropyl cellulose (trade name: HPC-SL, produced by Nippon Soda Co., Ltd.) was used instead of talc. Except for this, the somatic embryos were treated in the same manner as that in Example 1. As a result, agglomerations containing a multiplicity of somatic embryos were generated, and no powder-coated body having one somatic embryo in it was formed.

This is because hydroxypropyl cellulose dissolves in water instantly to become viscous solution so that it causes adherence.

[Example 2]

100 g of somatic embryos used in Example 1 and 400 g of soybean protein powder (trade name: Ajibron CZ, produced by Ajinomoto Co., Ltd.) were agitated in a V-type mixer with an internal capacity of 2 l rotated at 40 rpm for 3 minutes. Then, they were sieved by 250 micron mesh so as to remove excessive soybean powder, thereby obtaining powder-coated bodies. Each powder-coated body has a size slightly larger than that of the powder-coated body obtained in Example 1. Therefore, the powder-coated bodies obtained in this example could be easily dealt with and displayed the same performance as that in the case of Example 1.

[Example 3]

About 1 g of separated protocorm-like bodies of a cymbidium obtained by a culture method, as described in Fonnesbach, Physiol. Plant. 27: 360–364, (1972), were suspended in an isotonic liquid and were thereafter filtrated by a sieve of 350 micron. Micro-crystalline cellulose was sprinkled on this sieve while gently shaking the same by hand, thereby obtaining powder-coated bodies which were improved in mechanical strength and resistance to dryness and were easy to handle.

[Example 4]

Montmorillonite (trade name: HI-Fresh, produced by Soft Silica K.K.) was used instead of talc. Except for this, powder-coated bodies were obtained in the same manner as that in Example 1, and they displayed the same performance as that in the case of Example 1.

[Example 5]

Carnauba wax which had been finely pulverized was used instead of soybean protein. Except for this, powder-coated bodies were obtained in the same manner as that in Example 2, and they displayed the same performance as that in the case of Example 2.

[Example 6]

Carboxymethylcellulose calcium (trade name: ECG-505, produced by Gotoku Yakuhin K.K.) which had been finely pulverized was used instead of soybean protein. Except for this, powder-coated bodies were obtained in the same manner as that in Example 2, and they displayed the same performance as that in the case of Example 2.

The present invention has been described with respect to these examples, but the invention is not limited to these examples. Other modifications and alterations may be effected without departing from the spirit and scope of the present invention set forth in the appended claims.

For instance, the kinds of meristematic tissues and fine powder, the combinations of them, and the powder-coating conditions may be changed as desired. In the above description, only lactose is exemplified as a material with which powder-coated bodies formed in accordance with the present invention is coated, but it goes without saying that the powder-coated bodies can be used without further coating and that they may be coated with other substances.

The advantages of the present invention will be described below.

Powder-coated bodies in which meristematic tissues are independently contained can be formed under moderate conditions, so that each meristematic tissue is separated from each other and the strength and the size thereof are increased by the effect of adhered fine powder, thereby facilitating the handling of meristematic tissues. It is possible to maintain the water content of meristematic tissues and, hence, to prevent meristematic tissues from dying by dryness. Therefore, the present invention enables meristematic tissues to be dealt with on an industrial scale when further applying coating treatment or the like to the powder-coated bodies.

What is claimed is:

1. A powder coating method for separating into individual meristematic tissues an aggregate of at least two meristematic tissues comprising the step of mixing a fine powder which does not indicate adhesiveness during a mixing process with said aggregate of meristematic tissues which retain on their surface enough aqueous liquid to enable said fine powder to be adhered thereto and which can grow into entire plant bodies directly or after they have passed through differentiation and organogeniesis, thereby making said fine powder adhere to the periphery of said meristematic tissues.

2. A powder coating method according to claim 1, wherein said meristematic tissues are at least a type of tissues selected from a group constituted by somatic tissue, zygotic tissue and germ line tissue.

3. A powder coating method according to claim 2, wherein said somatic tissue is at least a type of tissue selected from a group constituted by definite bud, adventitious bud, somatic embryo, shoot primordium, multiple-shoot body, protocorm-like body and green spot.

4. A powder coating method according to claim 1, wherein said aqueous liquid is water or a liquid which mainly consists of water.

5. A powder coating method according to claim 1, wherein said fine powder is formed from at least one of a group of materials including minerals, inorganic salts, metals, oxides, metal hydroxides, ceramics, high-molecular compounds, solid wax and wax-like substances, carbon diatom earth and dried soil.

* * * * *